United States Patent [19]

Bobbitt et al.

[11] 4,056,519
[45] Nov. 1, 1977

[54] SUBSTRATE FOR ASSAY OF PLASMIN

[75] Inventors: Jesse L. Bobbitt; Edward L. Smithwick, Jr., both of Indianapolis, Ind.

[73] Assignee: Eli Lilly and Company, Indianapolis, Ind.

[21] Appl. No.: 685,193

[22] Filed: May 10, 1976

[51] Int. Cl.² .......................................... C07C 103/52
[52] U.S. Cl. .............................. 260/112.5 R; 424/9.4; 195/103.5 R; 23/230 B
[58] Field of Search .................................. 260/112.5 R

[56] References Cited

U.S. PATENT DOCUMENTS 3,862,011  1/1975  Smith .......................... 260/112.5 R Primary Examiner—Delbert R. Phillips
Attorney, Agent, or Firm—William C. Martens, Jr.; Everet F. Smith

[57] ABSTRACT

The proteinase plasmin is assayed either colorimetrically or fluorometrically with a tripeptidyl-4-methoxy-2-naphthylamide substrate having the following general formula:

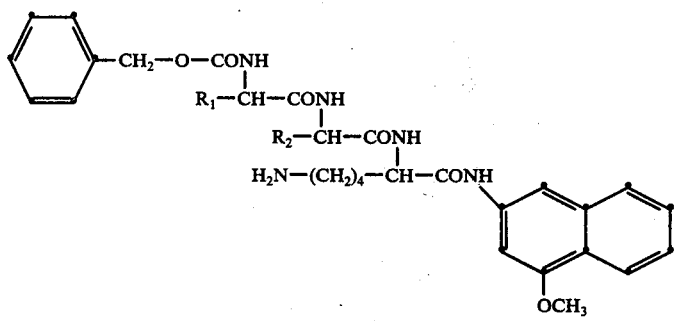

The substrate is useful for either routine clinical assays or kinetic studies.

5 Claims, No Drawings

SUBSTRATE FOR ASSAY OF PLASMIN

BACKGROUND OF THE INVENTION

This invention relates to plasmin. More particularly, this invention relates to a synthetic substrate for the colorimetric or fluorometric assay of plasmin.

In man, fibrinolysis is controlled and regulated by the activity of the plasminogen-plasmin proteolytic enzyme system. Plasminogen, the naturally occurring precursor, is converted to plasmin by naturally occurring plasminogen activators or by kinases, such as streptokinase, urokinase, and staphylokinase. Plasminogen, normally present in all body fluids and secretions, has its highest concentration in plasma.

In the prior art, plasmin assays typically involved protein digestion systems, with casein being the most commonly used protein. Although such systems were satisfactory to a limited extent, a number of disadvantages are inherent in such systems. In general, protein digestion systems require at least about 15 minutes per assay; during this period of time, it is not possible to measure kinetic changes (e.g., the instantaneous formation of plasmin). Furthermore, it is not possible to evaluate the presence of plasminogen activators. Additionally, at high plasmin levels, turbid solutions often result. More importantly, protein digestion systems are not entirely reproducible from one source of protein to another (hence, from one laboratory to another). Protein digestion systems require the use of an ultraviolet spectrophotometer, which poses problems in determining the appropriate blank since digestion of serum proteins in the blank contributes to ultraviolet absorption. Furthermore, plasmin content cannot be defined in the traditional manner of micromoles of substrate hydrolyzed per unit of time. That is, the hydrolysis is not linear with enzymatic activity; an arbitrary curve is obtained which must be defined by a standard enzyme solution of limited availability.

Attempts to overcome the disadvantages of protein digestion systems in the assay of plasmin have led to the preparation of a number of synthetic substrates. Examples of such synthetic substrates include, among others, the following: ethyl p-guanidinobenzoate hydrochloride and p-nitrophenyl p'-guanidinobenzoate hydrochloride [T. Chase, Jr. and E. Shaw, *Biochemistry*, 8, 2212 (1969)]; N-(p-carboxybenzyl)pyridinium bromide p-nitrophenyl ester [J. M. Sodetz and F. J. Castellino, *Biochemistry*, 11, 3167 (1972)]; N$^\alpha$-tosyl-L-arginine methyl, ethyl, and butyl esters, ethyl esters of glycine, L-lysine, DL-valine, L-leucine, L-isoleucine, DL-methionine, L-tyrosine, and DL-tryptophan, N$^\alpha$-benzoyl-L-arginine ethyl ester, N$^\alpha$-acetyl-L-tyrosine ethyl ester, N$^\alpha$-acetyl-DL-tryptophan ethyl ester, and N$^\alpha$-acetyl-DL-methionine ethyl ester [W. Troll, et al., *J. Biol. Chem.*, 208, 85 (1954)]; L-arginine methyl ester, L-lysine methyl ester, N$^\alpha$-acetyl-L-lysine methyl ester, N$^\alpha$-benzoyl-L-arginine methyl ester, N$^\alpha$-carbobenzoxy-L-lysine methyl ester, N$^\alpha$-tosyl-L-lysine methyl ester, N$^\alpha$-carbobenzoxy-L-arginine methyl ester, and N$^\alpha$-acetyl-L-arginine methyl ester [S. Sherry, et al., *Thromb. Diath. Haemorrh.*, 34, 20 (1975)]; N$^\alpha$-benzyloxycarbonyl-L-lysine p-nitrophenyl ester [R. M. Silverstein, *Thrombos. Res.*, 3, 729 (1973)]; N$^\alpha$-methyl-N$^\alpha$-tosyl-L-lysine β-naphthol ester [P. H. Bell, et al., *Anal. Biochem.*, 61, 200 (1974)]; and N$^\alpha$-benzoylphenylalanine-valine-arginine-p-nitroanilide [P. Friberger, et al., *Thromb. Diath. Haemorrh.*, 34, 321 (1975)]. The usual problems with most such synthetic substrates include, among others, a slow rate of reaction, rapid spontaneous hydrolysis, and difficulty in measuring the hydrolysis products.

It should be noted that some tripeptides are known which have the same amino acid sequences as the tripeptidyl portion of some of the substrates of the present invention. Examples of such known tripeptides include the following: N$^\alpha$-trityl-glycine-glycine-N$^\epsilon$-benzyloxycarbonyl-L-lysine benzyl ester, glycine-glycine-L-lysine, glycine-glycine-N$^\epsilon$-benzyloxycarbonyl-L-lysine benzyl ester hydrochloride, and N$^\alpha$-benzyloxycarbonyl-glycine-glycine-N$^\epsilon$-benzyloxycarbonyl-L-lysine benzyl ester and hydrazide [O. Abe, et al., *Bull. Chem. Soc. Japan*, 40, 1945 (1967)]; N$^\alpha$-formyl-L-phenylalanine-L-leucine-N$^\epsilon$-t-butyloxycarbonyl-L-lysine and methyl ester thereof [L. V. Ionova and E. A. Morozova, *J. Gen. Chem. USSR*, 34, 407 (1964)]; N$^\alpha$-benzyloxycarbonyl-glycine-glycine-L-lysine and diacetate monohydrate thereof [K. Suzuki and T. Abiko, *Chem. Pharm. Bull. (Tokyo)*, 16, 1997 (1968)]; and O-benzyl-N$^\alpha$-benzyloxycarbonyl-L-tyrosine-L-serine-N$^\epsilon$-t-butyloxycarbonyl-L-lysine methyl ester, N$^\alpha$,O-bis(-benzyloxycarbonyl)-L-tyrosine-L-serine-N$^\epsilon$-t-butyloxycarbonyl-L-lysine methyl ester, N$^\alpha$-benzyloxycarbonyl-L-tyrosine-L-serine-N$^\epsilon$-t-butyloxycarbonyl-L-lysine methyl ester, and L-tyrosine-L-serine-N$^\epsilon$-t-butyloxycarbonyl-L-lysine methyl ester [A. A. Costopanagiotis, et al., *J. Org. Chem.*, 33, 1261 (1968)].

The assay of plasmin by the plasmin-catalyzed hydrolysis of a given substrate to give one or more identifiable and measurable products is, of course, known in the art. The substrates of the present invention, however, can be used in such known procedure or procedures related thereto without the disadvantages attending the known, prior art substrates.

SUMMARY OF THE INVENTION

It therefore is an object of the present invention to provide a substrate for the assay of plasmin which eliminates or minimizes many of the problems associated with prior art protein digestion systems.

A further object of the present invention is to provide a substrate for the assay of plasmin which eliminates or minimizes many of the problems associated with prior art synthetic plasmin substrates.

Yet another object is to provide a sensitive, stable, versatile, substrate for the assay of plasmin which can be used with either colorimetric or fluorometric techniques. These and other objects will be apparent to those skilled in the art from a consideration of the specification and claims which follow.

In accordance with the present invention, a plasmin assay substrate is provided, which substrate is a tripeptidyl-4-methoxy-2-naphthylamide having the formula,

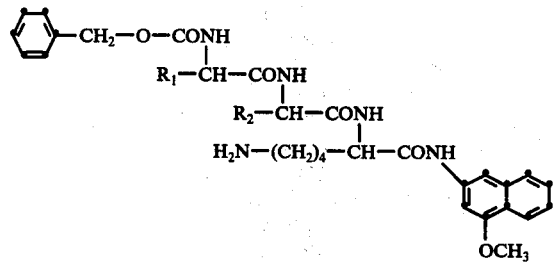

in which $R_1$ and $R_2$ independently are hydrogen, alkyl, hydroxyalkyl, mercaptoalkyl, methylthioalkyl, benzyl, or hydroxybenzyl, with the proviso that at least one of $R_1$ and $R_2$ must be other than benzyl or hydroxybenzyl; and the acid addition salts thereof in which the acid is inorganic or $C_1-C_2$ carboxylic.

It will be understood by those skilled in the art that reference to the assay of plasmin also includes the assay of plasminogen, since plasminogen is readily converted to plasmin by a small amount of activator, such as streptokinase, urokinase, and the like.

The substrates of the present invention are useful for either routine clinical plasmin or plasminogen assays or kinetic studies.

DETAILED DESCRIPTION OF THE INVENTION

As is well known in the art, all of the naturally-occurring amino acids, with the exception of glycine, are in the L form. To indicate this in the above-described general formula, the amino group (as a carboxylic acid amide) of each amino acid is placed above the carbon chain when the carbon chain is written horizontally with the carboxylic acid group (as the carboxylic acid amide) at the right. When reference is made herein to a specific tripeptidyl-4-methoxy-2-naphthylamide, the Tentative Rules of IUPAC-IUB Commission on Biochemical Nomenclature, Abbreviated Designation of Amino Acid Derivatives and Peptides, will be followed [see, e.g., J. Biol. Chem., 241, 2491 (1966)]; the 4-methoxy-2-naphthylamide portion will be indicated by the abbreviation, —MNA, and the N-blocking group, benzyloxycarbonyl, will be indicated by the abbreviation, Z-. In accordance with nomenclature already established by those skilled in the art, the peptidyl amides of 4-methoxy-naphthyl amine disclosed herein are named as tripeptidyl-4-methoxy-2-naphthylamides.

As already stated, $R_1$ and $R_2$ independently are hydrogen, alkyl, hydroxyalkyl, mercaptoalkyl, methylthioalkyl, benzyl, or hydroxybenzyl, with the proviso that at least one of $R_1$ and $R_2$ must be other than benzyl or hydroxybenzyl. Preferably, $R_1$ and $R_2$ independently are hydrogen or alkyl. More preferably, $R_1$ and $R_2$ both are either hydrogen or alkyl, and most preferably are alkyl. Examples of amino acids, other than lysine, which can be employed include, among others, glycine, alanine, valine, leucine, isoleucine, serine, threonine, cysteine, methionine, phenylalanine, and tyrosine.

Examples of specific tripeptidyl-4-methoxy-2-naphthylamides coming within the general formula described hereinabove include, among others, the following:

Z-Gly-Gly-L-Lys-MNA,
Z-L-Ala-L-Ala-L-Lys-MNA,
Z-L-Val-L-Val-L-Lys-MNA,
Z-L-Leu-L-Leu-L-Lys-MNA,
Z-L-Ile-L-Ile-L-Lys-MNA,
Z-L-Ser-L-Ser-L-Lys-MNA,
Z-L-Thr-L-Thr-L-Lys-MNA,
Z-L-Cys-L-Cys-L-Lys-MNA,
Z-L-Met-L-Met-L-Lys-MNA,
Z-Gly-L-Ala-L-Lys-MNA,
Z-Gly-L-Cys-L-Lys-MNA,
Z-L-Ala-Gly-L-Lys-MNA,
Z-L-Ala-L-Tyr-L-Lys-MNA,
Z-L-Val-L-Ser-L-Lys-MNA,
Z-L-Leu-L-Met-L-Lys-MNA,
Z-L-Ile-L-Ala-L-Lys-MNA,
Z-L-Ile-L-Thr-L-Lys-MNA,
Z-L-Ser-L-Ala-L-Lys-MNA,
Z-L-Ser-L-Phe-L-Lys-MNA,
Z-L-Thr-L-Ile-L-Lys-MNA,
Z-L-Cys-L-Val-L-Lys-MNA,
Z-L-Met-L-Cys-L-Lys-MNA,
Z-L-Met-L-Tyr-L-Lys-MNA,
Z-L-Phe-l-Thr-L-Lys-MNA,
Z-L-Tyr-Gly-L-Lys-MNA,
Z-L-Tyr-L-Met-L-Lys-MNA,
and the like.

Examples of the preferred compounds include, among others, Z-L-Ala-L-Ala-L-Lys-MNA, Z-L-Val-L-Val-L-Lys-MNA, Z-L-Leu-L-Leu-L-Lys-MNA, Z-L-Ile-L-Ile-L-Lys-MNA, Z-Gly-Gly-L-Lys-MNA, Z-Gly-L-Ala-L-Lys-MNA, Z-Gly-L-Ile-L-Lys-MNA, Z-L-Ala-Gly-L-Lys-MNA, Z-L-Ala-L-Leu-L-Lys-MNA, Z-L-Val-L-Ala-L-Lys-MNA, Z-L-Val-L-Ile-L-Lys-MNA, Z-L-Leu-Gly-L-Lys-MNA, Z-L-Leu-L-Val-L-Lys-MNA, Z-L-Leu-L-Ile-l-Lys-MNA, Z-L-Ile-L-Ala-L-Lys-MNA, Z-L-Ile-L-Leu-L-Lys-MNA, and the like. Examples of the more preferred compounds include, among others, Z-L-Ala-L-Ala-L-Lys-MNA, Z-L-Val-L-Val-L-Lys-MNA, Z-L-Leu-L-Leu-L-Lys-MNA, Z-L-Ile-L-Ile-L-Lys-MNA, Z-Gly-Gly-L-Lys-MNA, and the like. Examples of the most preferred compounds include, among others, Z-L-Ala-L-Ala-L-Lys-MNA, Z-L-Val-L-Val-L-Lys-MNA, Z-L-Leu-L-Leu-L-Lys-MNA, Z-L-Ile-L-Ile-L-Lys-MNA, and the like.

The tripeptidyl-4-methoxy-2-naphthylamide substrates provided by the present invention are prepared according to standard peptide chemistry procedures. The following examples are representative of such procedures:

EXAMPLE 1

Preparation of $N^\alpha$-Z-$N^\epsilon$-BOC-L-LYS-MNA

A mixture of 28.1 g. (50 mmol) of $N^\alpha$-Z-$N^\epsilon$-Boc-L-Lys as the N,N-dicyclohexylamine salt [prepared by the method of L. Zervas and C. Hamalidis, J. Amer. Chem. Soc., 87, 99 (1965)] and 17.25 g. (50 mmol) of 4-methoxy-2-naphthylamine p-toluenesulfonate [prepared by the procedure of E. L. Smithwick, Jr. and R. T. Shuman, synthesis, 8, 581 (1974)] in 100 ml. of N,N-dimethylformamide was agitated under a nitrogen atmosphere for 30 minutes. To the reaction mixture, cooled to 0° C., were added 6.75 g. (50 mmol) of 1-hydroxybenzotriazole and 10.3 g. (50 mmol) of N,N'-dicyclohexylcarbodiimide. After agitating for 2 hours at 0° C., the reaction mixture then was stirred at ambient temperature for 24 hours. The reaction mixture was cooled to 0° C. and the precipitated N,N'-dicyclohexylurea was removed by filtration. The filtrate was distilled under reduced pressure; the residue was triturated with 1 N aqueous sodium bicarbonate solution, then recrystallized three times from hot ethanol, giving 15.3 g. (58 percent) of $N^\alpha$-Z-$N^\epsilon$-Boc-L-Lys-MNA, m.p. 157°–159° C. The following elemental microanalysis was obtained:

Calculated for $C_{30}H_{37}N_3O_6$: C, 67.27; H, 6.96; N, 7.84
Found: C, 67.25; H, 6.74; N, 7.62.

EXAMPLE 2

Preparation of
$N^\alpha$-Z-L-Ala-L-Ala-$N^\epsilon$-Boc-L-Lys-MNA $N^\alpha$-Z-$N^\epsilon$-Boc-L-Lys-MNA (4.7 g., 8.8 mmol) was dissolved in 20 ml. of N,N-dimethylformamide and 50 ml. of ethanol, and subjected to hydrogenolysis over 1 g. of palladium on carbon at 1 atmosphere hydrogen pressure for 4 hours. The reaction mixture was filtered. The filtrate was concentrated under reduced pressure and the residue was dissolved in 30 ml. of N,N-dimethylformamide. To the resulting solution were added 8.8 mmol of $N^\alpha$-Z-L-Ala-L-Ala [prepared by the procedure of M. Goodman, et al., *Bioorg. Chem.*, 1, 294 (1971)], 1.19 g. (8.8 mmol) of 1-hydroxybenzotriazole, and 1.81 g. (8.8 mmol) of N,N'-dicyclohexylcarbodiimide. After standing 48 hours at 4° C., the reaction mixture was filtered to remove precipitated N,N'-dicyclohexylurea, and the filtrate was evaporated under reduced pressure. Trituration of the residue with 1 N sodium bicarbonate, followed by two recrystallizations from N,N-dimethylformamide/ethanol gave 3.5 g. (60 percent) of $N^\alpha$-Z-L-Ala-L-Ala-$N^\epsilon$-Boc-L-Lys-MNA, m.p. 213°-214° C. The following elemental microanalysis was obtained:

Calculated for $C_{36}H_{47}N_5O_8$: C, 63.79; H, 6.99; N, 10.33
Found: C, 64.05; H, 6.51; N, 10.63.

EXAMPLE 3

Preparation of $N^\alpha$-Z-L-Ala-L-Ala-L-Lys-MNA Acetate

A mixture of 3.0 g. (4.43 mmol) of $N^\alpha$-Z-L-Ala-L-Ala-$N^\epsilon$-Boc-L-Lys-MNA and 2.5 g. (3 meq) of p-toluene-sulfonic acid monohydrate in 100 ml. of acetonitrile containing 10 percent triethylsilane was agitated at ambient temperature for 8 hours. The reaction mixture was diluted with diethyl ether and the resulting precipitate was isolated by filtration. The precipitate was redissolved in N,N-dimethylformamide and extracted into chloroform after neutralization of the N,N-dimethylformamide solution with aqueous base. The chloroform was dried over anhydrous magnesium sulfate and evaporated in vacuo to give a residue which was lyophilized from acetic acid. The resulting residue then was dissolved in ethanol, treated with activated charcoal, and the product precipitated with diethyl ether, giving 1.5 g. (53 percent) of $N^\alpha$-Z-L-Ala-L-Ala-L-Lys-MNA acetate. The following amino acid analysis was obtained:

Ala, 2.03; Lys, 0.97 (92 percent recovery).

EXAMPLE 4

Preparation of $N^\alpha$-Z-Gly-Gly-$N^\epsilon$-Boc-L-Lys-MNA $N^\alpha$-Z-Gly-Gly-$N^\epsilon$-Boc-L-Lys-MNA was prepared from Z-Gly-Gly and $N^\epsilon$-Boc-L-Lys-MNA by the procedure of Example 2, then recrystallized from ethanol; m.p. 145°-147° C. The following elemental microanalysis was obtained:

Calculated for $C_{34}H_{43}N_5O_8$: C, 62.85; H, 6.67; N, 10.78
Found: C, 62.62; H, 6.42; N, 10.56

EXAMPLE 5

Preparation of $N^\alpha$-Z-Gly-Gly-L-Lys-MNA Acetate $N^\alpha$-Z-Gly-Gly-L-Lys-MNA acetate was prepared from the compound of Example 4 by the procedure of Example 3. The following amino acid analysis was obtained:

Gly, 1.98; Lys, 1.02 (74 percent recovery).

As already stated, the substrates of the present invention are useful for the determination of plasmin. Plasminogen, the plasmin precursor, normally has its highest concentration in plasma, which concentration depends upon the physical well-being of the individual. Since plasminogen concentration, and, consequently, plasmin concentration, are altered by various fibrinolytic disorders, the monitoring of plasmin concentration in plasma provides a means for the detection of fibrinolytic disorders and for monitoring the clinical treatment of such disorders as is well known in the art.

In general, the plasmin assay employing the substrates of the present invention is carried out in accordance with known procedures. Briefly, from about 0.1 ml. to about 0.5 ml., preferably from about 0.1 to about 0.2 ml., of blood plasma is diluted to a volume of 1.5 ml. with 0.05 molar tris(hydroxymethyl)aminomethane (Tris) buffer at pH 8.0. If plasminogen is to be determined, 500–1000 International Units of streptokinase is added to the blood plasma sample before diluting with the Tris buffer. To the diluted blood plasma solution is added 1.0 ml. of an aqueous substrate solution containing 1.2 mg. (2 mM) of substrate per ml. of water. The resulting reaction mixture then is incubated, typically for 15 minutes at 37° C. For a fluorometric assay, the reaction solution is transferred immediately after incubation to a fluorometer and light of 360 nm wavelength is used for excitation; the relative intensity of fluorescence at 420 nm is measured. For colorimetric assay, the reaction is stopped after incubation by the addition of 0.1 ml. 1.0 N aqueous hydrochloric acid solution. To the reaction solution then is added 1 ml. of fast blue B dye solution containing 1 mg. of dye. Color is allowed to develop, typically for 5 minutes at ambient temperature, and absorbance then is measured at 520 nm. If desired, instantaneous measurements of plasmin activity can be made by transferring the reaction mixture, without incubation, immediately to a fluorometer and recording the increase of fluorescence with time.

The results obtained from either the colorimetric or fluorometric assay are compared with plasmin standard curves which are prepared in accordance with known procedures. The plasmin standard curves employed to obtain the data reported herein were made with "First British Standard for Plasmin, Human, 72/739," obtained from the National Institute for Biological Standards and Control, Holly Hill, Hampstead, London. Fast blue B dye was purchased from K and K Laboratories, Plainview, N.Y.

Colorimetric measurements were made with Gilford Spectrophotometers, either Model 300-N or Model 240 with a digital absorbance meter (Model 410) and recorder (Model 6040). Absorption spectra were determined with a Cary 14 Recording Spectrophotometer. Fluorescence measurements were made with an Aminco-Bowman Spectrophotofluorometer with a Xenon lamp ratio photometer and a Shimadzu recorder, Model R-101.

The use of the above-described procedure to assay plasmin and plasminogen is illustrated by the data in Table 1. Such data were obtained by the preferred 15-minute colorimetric assay, using as substrate Z-L-Ala-L-Ala-L-Lys-MNA. The streptokinase, when used, was added to the blood plasma sample, prepared in the usual way, prior to dilution with Tris buffer. While any plasmin already present will be measured along with plasmin derived from plasminogen, it usually is not necessary to correct the plasminogen value for plasmin when normal subjects are used, since the blood plasma of such subjects typically contains negligible amounts of plasmin.

Table 1
Colorimetric Plasminogen and Plasmin Assays of Blood Plasma from Normal Subjects, Using Z-L-Ala-L-Ala-L-Lys-MNA As Substrate

| Sample | Plasma Vol., ml. | Units SK[a] | $A_{520}$ | Plasminogen, Units/ml. | Plasmin, Units/ml. |
|---|---|---|---|---|---|
| A. Human Plasma | | | | | |
| Patient 1 | 0.1 | 1000 | 0.12 | 1.2 | — |
| Patient 2 | 0.1 | 1000 | 0.18 | 1.8 | — |
| Patient 3 | 0.2 | 1000 | 0.36 | 1.8 | — |
| B. Dog Plasma | | | | | |
| Sample 1 | 0.1 | 500 | 0.096 | 1.0 | — |
| Sample 2 | 0.1 | 500 | 0.085 | 0.8 | — |
| Sample 2 | 0.1 | 0 | 0.005 | — | <0.05 |

[a]SK = Streptokinase

All enzyme contents are expressed in the internationally defined units which are well known to those skilled in the art. It may be noted from Table 1 that the approximate lower limit of detection of plasmin is 0.05 unit/ml. The limit is to a large extent the result of instrumental error at low absorbance values. Thus, when plasmin content is known to be low, larger plasma samples should be employed.

The colored compound formed by the reaction of 4-methoxy-2-naphthylamine with fast blue B dye has a strong absorption band at 520 nm. The molar absorption coefficient, $\epsilon$, decreases with time and exposure to light, and concentrated solutions, i,e., solutions giving an absorbance through a 1 cm. cell greater than about 1.0, fade and frequently form a precipitate. Fading and precipitation are accelerated by exposure to light. The maximum value for $\epsilon$ obtained by using a dilute solution and development of color in the dark, is about 33,000 $M^{-1} cm^{-1}$. Although maximum color is not achieved in light, it is more convenient to let the color develop under ordinary room illumination and to read absorption values consistently five minutes after adding dye to the assay sample. Under such conditions, the value for $\epsilon$ is about 27,000 $M^{-1} cm^{-1}$. Except as discussed above, the value for $\epsilon$ in either case in constant for any given amine-dye coupling product and is independent of the tripeptidyl moiety.

In general, the assay can be carried out at a pH of from about 7 to about 10. The optimum pH, however, is from about 8 to about 8.5, with pH 8.0 being most preferred.

The relationship of absorbance or intensity of fluorescence to plasmin concentration typically is linear, provided that plasmin concentration is less than about 1.0 unit of plasmin per assay volume (typically about 3.5 ml.) and the incubation time is no greater than about 15 minutes. The linearity of such relationship is preserved, however, at longer incubation times, e.g., up to about 60 minutes, when plasmin concentration is less than about 0.2 unit plasmin per assay volume. Accordingly, it is preferred to use sample sizes which will provide less than about 1 unit of plasmin per assay volume and incubation periods of 15 minutes.

In order to study the effectiveness of the substrates provided by the present invention, colorimetric plasmin assays were run using solutions containing known quantities of plasmin in place of blood plasma samples. Plasmin was obtained by converting plasminogen to plasmin by the addition of either streptokinase or urokinase to a plasminogen-containing solution. The plasminogen was prepared from outdated human plasma by batch absorption on lysine-Sepharose, entirely under cold conditions; see R. J. Walther, et al., J. Biol. Chem., 249 1173 (1974), and D. K. McClintock, et al., Biochemistry, 13, 5334 (1974). Steptokinase was obtained as Varidase from Lederle, Pearl River, N.Y., and urokinase was obtained from Leo Pharmaceutical Products, Denmark. The colorimetric assay results obtained with such known plasmin solutions are summarized in Table 2.

TABLE 2
Hydrolysis of Plasmin Substrates

| Substrate | Units Plasmin | $A_{520}$ | nmoles Hydrolyzed /unit plasmin |
|---|---|---|---|
| Z-Gly-Gly-L-Lys-MNA | 10 | 1.2 | 16 |
| Z-L-Ala-L-Ala-L-Lys-MNA | 2 | 1.8 | 120 |

Plasmin content is expressed in the internationally defined units which are well known to those skilled in the art. From the last or right-hand column of Table 2, it is seen that of the two substrates tested, Z-L-Ala-L-Ala-L-Lys-MNA is the more sensitive toward hydrolysis by plasmin. Thus, such substrate will be the more effective for determinations involving low plasmin concentrations.

While the substrates of the present invention are not specific for plasmin, such substrates do possess a sufficient degree of specificity for plasmin that the plasmin assay can be carried out in the presence of small amounts of other, related enzymes. Such specificity is shown in Table 3, which summarizes the hydrolysis, determined by the colorimetric procedure, of Z-L-Ala-L-Ala-L-Lys-MNA by plasmin and several other proteinases. Trypsin was obtained from Worthington Biochemical Corporation, Freehold, New Jersey; thrombin was purchased from Parke, Davis, and Company, Detroit, Michigan; and procine acrosin was obtained from Dr. P. J. Burck of the Lilly Research Laboratories, Indianapolis, Ind. Except as footnoted in Table 2, all amounts of enzymes are expressed in internationally defined units.

TABLE 3
Hydrolysis of Z-L-Ala-L-Ala-L-Lys-MNA by Proteinases

| Enzyme | Units Per Test | nmoles Hydrolyzed | Units Per mole of Enzyme | mole Hydrolyzed per mole of Enzyme |
|---|---|---|---|---|
| Thrombin | 100 | 74 | $8.5 \times 10^{10}$ | 63 |
| Acrosin | 400 | 23 | $1.2 \times 10^{12}$ | 69 |
| Urokinase | 400 | 9 | $3.8 \times 10^{12}$ | 86 |
| Plasmin | 1 | 120 | $3.4 \times 10^9$ | 340 |
| Trypsin | 2[a] | 290 | $24 \times 10^9$ | 3500 |

[a]1 unit - 1 $\mu$g

The data in both Tables 2 and 3 were obtained in accordance with the preferred 15-minute colorimetric plasmin assay described hereinbefore. As already stated, Table 3 is an illustration of the relative order of specificity of several proteinases toward Z-L-Ala-L-Ala-L-Lys-MNA, one of the substrates of the present invention. The data in Table 3 were obtained by subjecting the substrate to hydrolysis by each enzyme. The nmoles of substrate hydrolyzed in each case were determined from the absorbance value in the usual manner. The nmoles of substrate hydrolyzed then were converted to moles of substrate hydrolyzed per mole of enzyme, using the generally accepted value, taken from the literature, for the number of units per mole of each enzyme.

The relatively low values for moles of substrate hydrolyzed per mole of enzyme for thrombin, acrosin, and urokinase demonstrate that the presence of small amounts of such enzymes will not significantly interfer with the plasmin assay. The enzyme trypsin, however, is known to be both potent and of a broad specificity, requiring only the presence of a basic amino acid. Therefore, the rapid hydrolysis of trypsin of the substrate of Table 2 was expected. Trypsin, however, normally is not present in the blood and hence presents no problem in the plasmin assay.

The substrates of the present invention provide the means for plasmin assays which are reproducible, sensitive, and convenient. The sensitivity of the assay results more from the sensitivity in detecting hydrolysis than from the kinetics of the reaction; hence, blank corrections for the substrates of the present invention are negligible. The high molar absorptivity of the dye complex and the intensity of the fluorescence facilitate detection of small amounts of hydrolysis product.

It should be pointed out that substrate solubility must be taken into consideration when carrying out plasmin assays with such substrates. The assay as described uses a substrate concentration of about 2 mM. This does not cause problems so long as the substrate concentration is consistent and assays are restricted to the linear part of the rate curve. If necessary, the concentration of such substrate can be doubled, thereby approaching the limits of solubility of the substrate, to obtain a slight increase in sensitivity and an extension of the range of the linearity. Beyond that, substrate insolubility becomes a problem. The substrate also is less soluble in buffer of ionic strength greater than 0.1. Protein also precipitates the substrate, but the assay has been used to measure serum plasma levels without difficulty.

Since substrate solubility can be important, it often is desirable to employ an acid addition salt of the substrate in order to improve substrate solubility. The term "acid addition salt" is well known to those skilled in the art. In general, such a salt is formed by reacting in a mutual solvent a stoichiometric amount of a suitable acid with a substrate of the present invention, although an excess of the acid can be used where the acid is sufficiently volatile. Normally, the choice of salt-forming acid is not critical. Representative and suitable acids include, among others, the following: hydrochloric, hydrobromic, hydriodic, sulfuric, nitric, phosphoric, formic, acetic, and the like.

The chief advantage of the substrates of the present invention are in the versatility of the plasmin assay employing such substrates. A large number of routine assays are easily handled by the colorimetric procedure. Very sensitive measurements can be made by fluorometry. Kinetic analyses of plasmin activity can be made to avoid problems of enzyme stability. The substrates of the present invention also are useful in the identification of enzyme activity on electropherograms, using either fluorometric or colorimetric techniques.

What is claimed is:

1. A tripeptidyl-4-methoxy-2-naphthylamide having the formula,

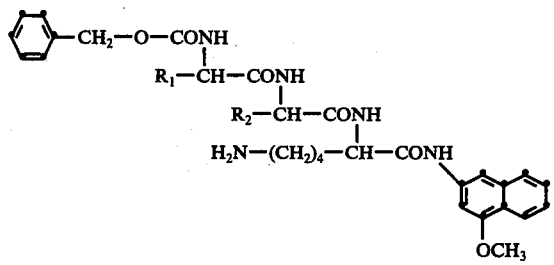

in which $R_1$ and $R_2$ independently are hydrogen, alkyl, hydroxyalkyl, mercaptoalkyl, methylthioalkyl, benzyl, or hydroxybenzyl, with the proviso that at least one of $R_1$ and $R_2$ must be other than benzyl or hydroxybenzyl; and the acid addition salts thereof in which the acid is inorganic or $C_1$-$C_2$ carboxylic.

2. The compound of claim 1 in which $R_1$ and $R_2$ independently are hydrogen or alkyl.

3. The compound of claim 1, in which $R_1$ and $R_2$ are the same and are alkyl.

4. The compound of claim 2, in which $R_1$ and $R_2$ are hydrogen.

5. The compound of claim 3, in which $R_1$ and $R_2$ are methyl.

* * * * *